US008628496B2

(12) United States Patent
Valaie (10) Patent No.: US 8,628,496 B2
(45) Date of Patent: Jan. 14, 2014

(54) LOW PROFILE INTRODUCER APPARATUS

(75) Inventor: Arman H. Valaie, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 0 days.

(21) Appl. No.: 13/424,938

(22) Filed: Mar. 20, 2012

(65) Prior Publication Data

US 2012/0245526 A1    Sep. 27, 2012

Related U.S. Application Data

(63) Continuation of application No. 11/440,834, filed on May 25, 2006, now Pat. No. 8,152,767.

(60) Provisional application No. 60/685,188, filed on May 27, 2005.

(51) Int. Cl.
*A61M 5/178* (2006.01)
*A61F 11/00* (2006.01)

(52) U.S. Cl.
USPC .......................................... 604/158; 606/108

(58) Field of Classification Search
USPC ..................... 606/108; 604/145; 600/184
See application file for complete search history.

(56) References Cited

U.S. PATENT DOCUMENTS

| 4,306,562 A | 12/1981 | Osborne .................... 128/348 |
| 4,404,159 A | 9/1983 | McFarlane ................. 264/296 |
| 4,405,314 A | 9/1983 | Cope ............................. 604/51 |
| RE31,855 E | 3/1985 | Osborne ..................... 604/161 |
| 4,581,025 A | 4/1986 | Timmermans ............. 604/264 |
| 4,629,450 A | 12/1986 | Suzuki et al. ............... 604/164 |
| 4,650,472 A | 3/1987 | Bates ........................... 604/158 |
| 4,842,582 A | 6/1989 | Mahurkar ..................... 604/43 |
| 5,011,478 A | 4/1991 | Cope ............................ 604/165 |
| 5,292,311 A | 3/1994 | Cope ............................ 604/165 |
| 5,499,975 A | 3/1996 | Cope et al. .................. 604/165 |
| 5,830,227 A | 11/1998 | Fischell et al. ............. 606/194 |
| 6,053,904 A | 4/2000 | Scribner et al. ............. 604/527 |
| 2001/0047154 A1 | 11/2001 | Jepson et al. ........... 604/167.01 |
| 2005/0004523 A1 | 1/2005 | Osborne et al. ......... 604/164.01 |

FOREIGN PATENT DOCUMENTS

| AU | 34781/84 | 5/1988 |
| AU | 47657/90 | 5/1993 |
| CA | 1223829 | 7/1987 |
| EP | 0 162 982 B1 | 7/1989 |
| EP | 0 778 045 A2 | 6/1997 |
| EP | 1 092 449 A1 | 4/2000 |
| JP | 3-65191 | 11/1999 |
| WO | WO 93/02735 A1 | 2/1993 |
| WO | WO 2005/004967 A2 | 1/2005 |

OTHER PUBLICATIONS

Silhouette™ Transitionless Peel-Away® Introducers, brochure from Cook Incorporated, Copyright 1999, 1 pg.

*Primary Examiner* — Gary Jackson
*Assistant Examiner* — Michael Mendoza
(74) *Attorney, Agent, or Firm* — Brinks Gilson & Lione (57) ABSTRACT

An introducer apparatus includes an outer sleeve and an inner cannula received within the lumen of the outer sleeve. The outer sleeve has a profile such that at least a portion of the distal end of the outer sleeve tapers in the distal direction at an angle not exceeding about 2° relative to a longitudinal axis of the apparatus. The distal open end of the outer sleeve has a wall thickness not exceeding about 0.003 inch. The inner cannula includes a tapered distal end portion. The tapered distal portion of the inner cannula extends distal to the distal open end of the outer sleeve, such that a generally smooth diametrical transition is provided between the outer sleeve tapered portion and the open distal end of the inner cannula.

22 Claims, 7 Drawing Sheets

INVENTIVE APPARATUS - SPECIMENS 1-15

FIGURE 9

INVENTIVE APPARATUS - SPECIMENS 16-30

FIGURE 10

PRIOR ART APPARATUS - SPECIMENS 1-15

FIGURE 11

PRIOR ART APPARATUS - SPECIMENS 16-30

LOW PROFILE INTRODUCER APPARATUS

RELATED APPLICATION

The present application is a Continuation Application of U.S. Application Ser. No. 11/440,834, now U.S. Pat. No. 8,152,767, filed on May 25, 2006 which claims priority to U.S. Provisional application No. 60/685,188 filed on May 27, 2005, the entire contents of which is herein incorporated by reference.

BACKGROUND

1. Technical Field

The present invention relates to the field of introducer assemblies for providing percutaneous access to the vascular system. More specifically, the invention relates to a low profile apparatus suitable for introducing catheters and other interventional devices into the vascular system with a minimal amount of trauma to the patient.

2. Background Information

Many medical procedures require the percutaneous placement of an interventional medical device, such as a catheter, into an artery or vein. Such interventional devices may be used for, among other things, blood pressure monitoring, blood sampling, and the administration of fluids and medicaments to a patient.

Typically, such devices are introduced into the vascular system using the well-known Seldinger percutaneous entry technique. In the Seldinger technique, the physician makes an oblique entry into the artery or vein with a beveled needle. A wire guide is passed through the bore of the needle into the artery or vein. The needle is thereafter withdrawn, leaving the wire guide in place. The catheter or other interventional device is then passed over the wire guide, through the puncture, and into the artery or vein at the needle puncture site. Once the catheter is in place, the wire guide can be withdrawn.

One of the disadvantages of this procedure is that the initial needle stick must normally be made with a needle that is large enough to accept the wire guide through its central bore. Conventional wire guides often comprise a tightly wound helical stainless steel wire coil. In order to have sufficient rigidity to properly support and lead many standard catheters and other interventional devices in common use in modern medicine, such wire guides are typically constructed to have an outer diameter in the range of about 0.035 to 0.038 inch (0.89 or 0.97 mm). This diameter of wire guide will typically pass through an 18 gauge thinwall needle. An 18 gauge needle typically has a 0.050 inch (1.27 mm) outer diameter (O.D.) and a 0.042 inch (1.07 mm) inner diameter (I.D.).

The 18 gauge needle is the most common sized needle used for initial vascular access, and has become a standard needle for use with the Seldinger technique for percutaneous catheterization. However, the O.D. of an 18 gauge needle is just large enough to damage tissue or cause excessive bleeding if it does not enter the vessel correctly, or if it inadvertently penetrates an organ or other unintended body structure. As a result, it is desirable to utilize a smaller gauge needle, such as a 21 gauge thinwall needle, for initial entry. A 21 gauge thinwall needle typically has a 0.032 inch (0.81 mm) O.D. and a 0.022 inch (0.56 mm) I.D., or smaller. Needles of 21 gauge thinwall, or smaller, are considered small enough that they do not damage tissue or organs, or cause excessive bleeding if inserted off target. In addition, smaller gauge needles generally have correspondingly shorter bevels at the needle tip compared to the size of the bevel tip of an 18 gauge needle. Thus, it is much easier to get a short bevel into the lumen of a small vessel than the longer bevel of the 18 gauge needle.

Unfortunately, the bore of a needle of 21 gauge, or smaller, is not large enough to enable a standard 0.035 inch or 0.038 inch (0.89 mm or 0.97 mm) diameter wire guide to be passed therethrough. The largest wire guide that can be easily introduced into such small gauge needles is normally a wire of 0.018 inch (0.46 mm) O.D. However, many diagnostic and interventional devices need at least a 0.035 inch (0.89 mm), and more preferably a 0.038 inch (0.97 mm), diameter wire guide to provide sufficient support to enable the physician to optimally introduce and manipulate the device through the vasculature over the wire. Thus, unless a larger diameter wire guide is introduced into the vasculature, many such devices cannot be successfully introduced.

U.S. Pat. No. 4,650,472 describes an apparatus which enables a physician to introduce a medical device, such as a catheter, into the body of a patient by making the initial puncture with a small gauge needle, such as a 22 gauge (0.028 inch; 0.72 mm O.D.) needle, in place of the larger conventional 18 gauge needle. The '472 patent is incorporated by reference herein. A 0.018 inch (0.46 mm) outer diameter wire guide is initially inserted through the bore of the small gauge (e.g. 22 gauge) needle. The needle is thereafter withdrawn, and a removable inner cannula, or dilator, is provided over the wire guide but inside an outer sleeve portion of the catheterization apparatus. This removable inner cannula has a tapered tip, and provides a transition between the large distal opening of the outer sleeve and the 0.018 inch wire guide. The inner cannula is generally about 0.038 inch (0.97 mm) O.D., and the outer sleeve is sized to fit over the inner cannula.

The outer sleeve and the inner cannula of the apparatus disclosed in the '472 patent are normally inserted into the blood vessel in tandem. The diametrical transition of the leading end of this tandem is intended to minimize the trauma that may otherwise be caused by the insertion of a large diameter outer sleeve over a small diameter wire guide. Once the outer sleeve is properly positioned within the blood vessel, the inner cannula and the smaller wire guide can be withdrawn, leaving the outer sleeve in place. A larger (0.035 to 0.038 inch) (0.89 to 0.97 mm) wire guide can then be introduced through the outer sleeve and into the vessel. If desired, the outer sleeve can thereafter be removed from the patient, leaving the larger wire guide in the vessel ready to accept a catheter or other interventional device. The apparatus of the '472 patent has been successfully used to percutaneously insert a medical device, such as a catheter, having a large outer diameter into a blood vessel when the initial insertion is made with an introducer needle and a wire guide which are much smaller in diameter than the distal opening of the catheter.

The apparatus of the '472 patent thus enables the physician to introduce larger diagnostic and interventional devices into a vessel than would otherwise be possible in a procedure in which initial vessel entry has been made with a small gauge needle. When the apparatus is inserted into the vessel as described, however, the physician must exert sufficient force to overcome the resistance provided at the "bump" that is present at the transition between the distal end of the outer sleeve and the underlying portion of the inner cannula. If this force is not carefully controlled, the physician may inadvertently exert too great a force to overcome the bump, and thereby puncture the side of the vessel opposite the initial stick. Thus, although the device of the '472 patent may be successfully used to introduce large devices when initial entry is made with a small gauge needle, it is nonetheless desired to further improve this device, by providing a design which reduces the amount of force required to insert the outer sleeve into the vessel, and thereby reduces the possibility of an inadvertent puncture of the opposing vessel wall.

BRIEF SUMMARY

The problems of the prior art are addressed by the apparatus and method of the present invention.

In one form thereof, the invention comprises an introducer apparatus comprising an outer sleeve and an inner cannula. The outer sleeve has a lumen extending longitudinally therethrough, and has a profile such that at least a portion of the outer sleeve tapers toward the outer sleeve distal end at an angle not exceeding about 2° relative to a longitudinal axis of the apparatus. The outer sleeve has a distal open end sized such that a first wire guide is receivable therethrough. The distal open end of the outer sleeve has a wall thickness not exceeding about 0.003 inch. The inner cannula has a lumen extending longitudinally therethrough, and is sized to be received within the lumen of the outer sleeve. The inner cannula has a portion that tapers toward the inner cannula distal end. The inner cannula distal open end is sized such that a second wire guide is receivable therethrough, and the first wire guide is not receivable therethrough. The tapered distal portion of the inner cannula extends distal to the distal open end of said outer sleeve, and has a profile such that a generally smooth diametrical transition is provided between the outer sleeve tapered portion and the inner cannula open end.

In another form thereof, the invention comprises a method of inserting a wire guide into a body vessel of a patient for use in introducing a medical interventional device thereover. An introducer system comprises an introducer needle having an inner bore that does not exceed about 0.018 inch (0.46 mm) in diameter; a first wire guide having an outer diameter not less than about 0.035 inch (0.89 mm); a second wire guide having an outer diameter not greater than about 0.018 inch (0.46 mm) and being receivable in a bore of the introducer needle; and an introducer apparatus comprising an outer sleeve and an inner cannula. The inner cannula is removably received in a lumen of the outer sleeve. The outer sleeve has a profile such that a distal portion of the sleeve tapers toward the sleeve distal end at an angle not exceeding about 2° with a longitudinal axis of the sleeve. The outer sleeve distal open end is sized such that the first wire guide is receivable therethrough. The inner cannula has a lumen extending therethrough, and has a distal portion that tapers toward the inner cannula distal end. The inner cannula distal open end is sized such that the second wire guide is receivable therethrough and the first wire guide is not receivable therethrough. The tapered distal portion of the inner cannula extends distal to the distal open end of the outer sleeve, and has a profile such that a generally smooth diametrical transition is provided between the outer sleeve tapered portion and the inner cannula open end. The needle is injected into the body vessel, and the second wire guide is inserted through the needle bore such that a distal end of the wire guide extends beyond the needle in the body vessel. The needle is withdrawn from the body vessel over the second wire guide, ant the introducer apparatus is thereafter introduced over the wire guide such that the respective distal ends of the outer sleeve and inner cannula are in the body vessel. The second wire guide is withdrawn from the introducer apparatus while maintaining the introducer apparatus in the body vessel. The inner cannula is separated from the outer sleeve, and removed from the vessel while maintaining the outer sleeve in the body vessel. The first wire guide is guided through the outer catheter such that a distal end of the first wire guide extends beyond the outer sleeve in the body vessel. The outer cannula may then be withdrawn over the first wire guide.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial ends of the inventive apparatus, as well as the axial ends of various related components. The term "proximal" is used in its conventional sense to refer to the end of the apparatus (or component) that is closest to the operator during use of the collar. The term "distal" is used in its conventional sense to refer to the end of the apparatus (or component) that is initially inserted into the patient, or that is in closest proximity to the patient.

Figure 1:
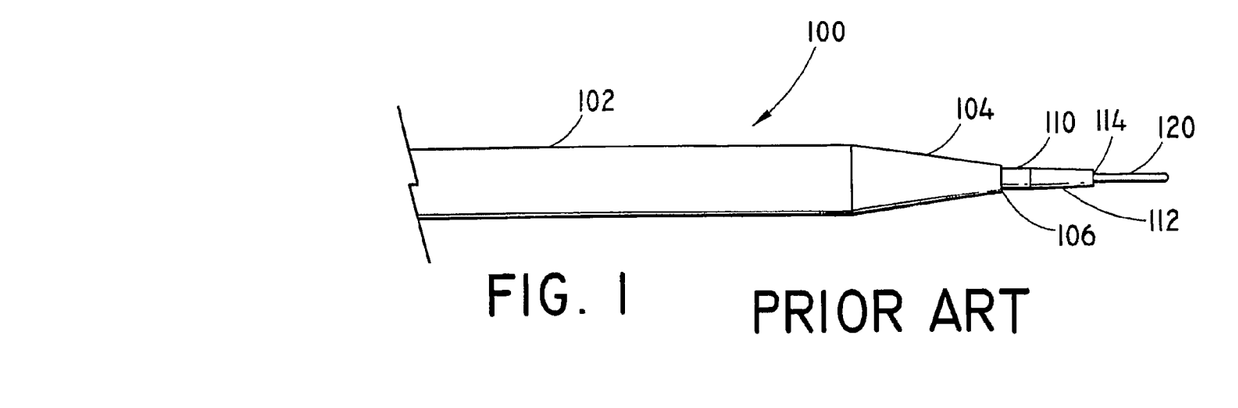
FIG. 1 is a side view of the distal end portion of a prior art introducer apparatus suitable for entry into the vascular system with a small gauge needle.

FIG. 1 is a side view of the distal end portion of a prior art introducer apparatus 100 for introducing a medical device into a body vessel when the initial stick is made with a small gauge needle. Introducer apparatuses of this type are further described in the incorporated-by-reference U.S. Pat. No. 4,650,472. FIG. 1 illustrates a typical dimensional relationship between an outer sleeve 102, inner cannula 110 and small diameter wire guide 120. Outer sleeve 102 includes a distal portion 104 that tapers to outer sleeve distal end 106. Inner cannula 110 also includes a distal portion 112 that tapers to inner cannula distal end 114. In the example shown, wire guide 120 extends from inner cannula distal end 114 in the normal fashion.

Figure 2:
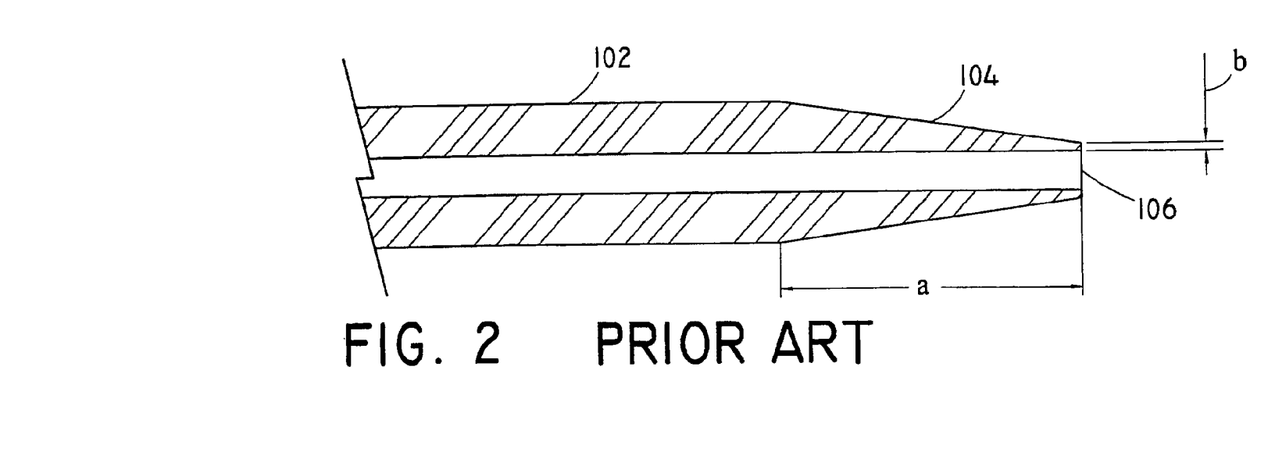
FIG. 2 is an enlarged sectional view of the outer sleeve of the apparatus of FIG. 1.

FIG. 2 is an enlarged sectional view of outer sleeve 102 of prior art apparatus 100. Generally, for an outer sleeve having a typical outer diameter of about 5 French and a length of about 10 cm or more, the length a of tapered portion 104 in this prior art apparatus is approximately 4 (±1) mm. The thickness b of the wall of sleeve 102 at distal end 106 is about 0.004 (±0.0005) inch [0.10 (±0.013) mm]. Tapered area 104 extends at an angle of greater than about 3°, typically greater than 3.5° from a longitudinal axis.

Figures 3, 4, 5:
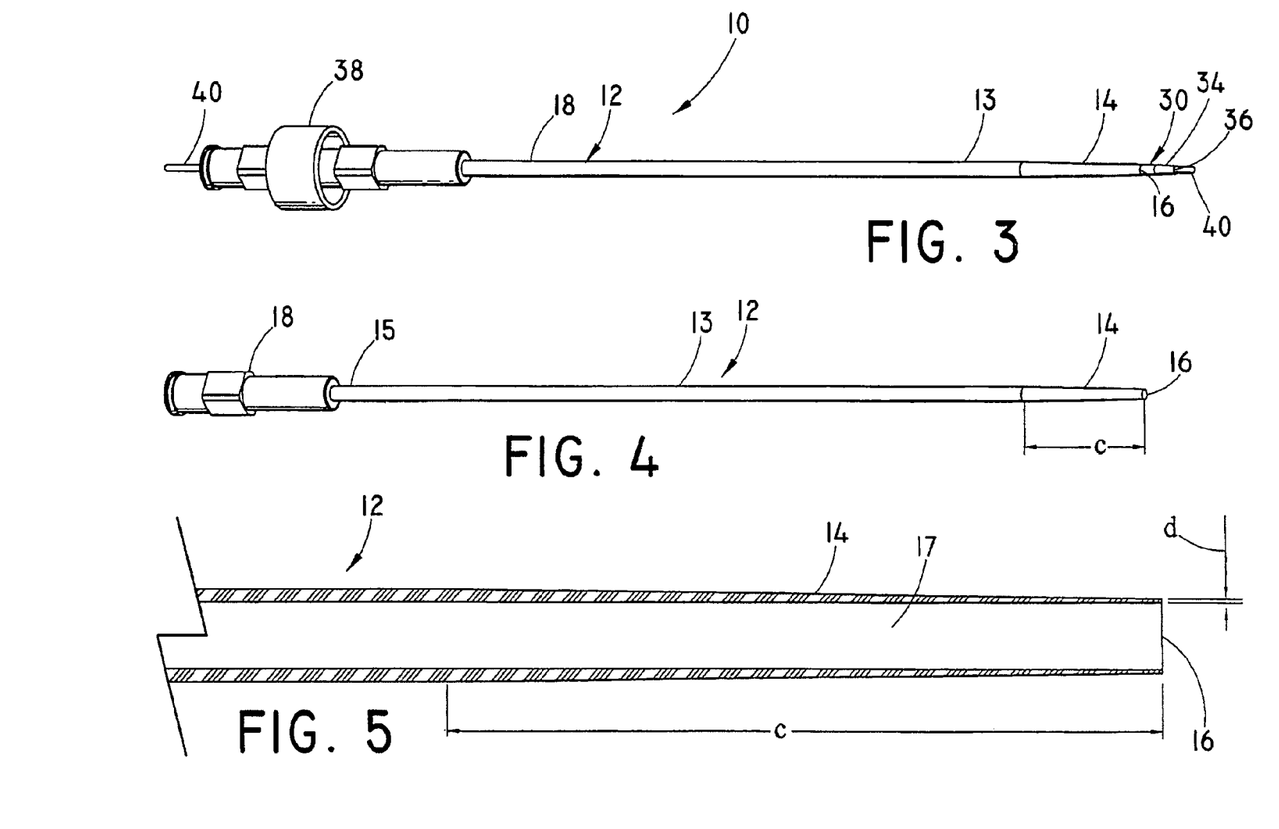
FIG. 3 illustrates one embodiment of a low profile introducer apparatus of the present invention.
FIG. 4 illustrates a side view of the outer sleeve of the low profile introducer apparatus of FIG. 3.
FIG. 5 illustrates an enlarged distal end portion of the outer sleeve shown in FIG. 4.

FIG. 3 illustrates one embodiment of an introducer apparatus 10 of the present invention. Introducer apparatus 10 comprises an outer sleeve 12 and an inner cannula 30 that extends through a lumen 17 (FIG. 5) in the outer sleeve. A small diameter wire guide 40 extends through a lumen (not shown) in inner cannula 30. Outer sleeve 12 is further illustrated in FIG. 4, and inner cannula 30 is further illustrated in FIG. 6. FIG. 5 is an enlarged view of the distal end portion of outer sleeve 12.

Figure 7:
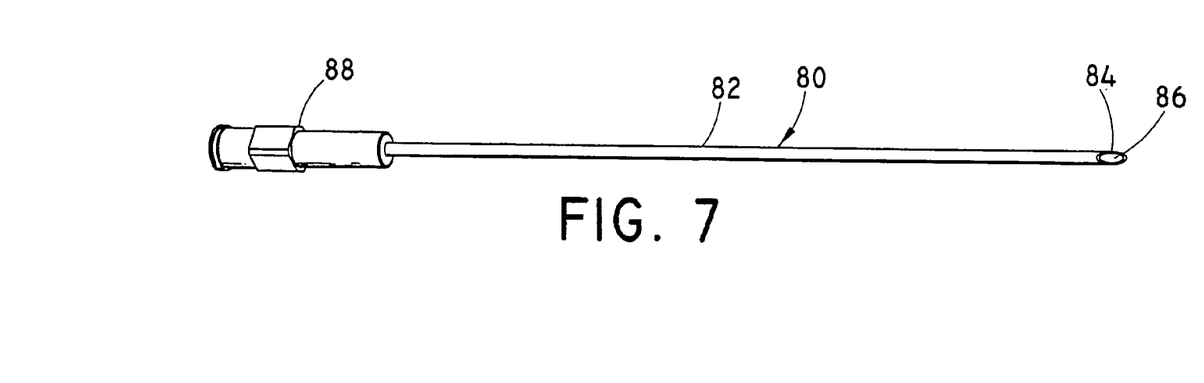
FIG. 7 is a side view of a small gauge needle suitable for use in connection with the low profile introducer apparatus of the present invention.

Like the prior art structure shown in FIGS. 1 and 2, apparatus 10 may be used for introducing a medical device into a body vessel using a small gauge needle, e.g., a needle of 21 gauge or smaller. One example of a suitable small gauge needle 80 is shown in FIG. 7. Needle 80 is a conventional small gauge needle, and includes a stainless steel shaft 82 having a lancet beveled tip 84, and a lumen 86 therethrough. A standard hub 88 may be attached at the proximal end of needle 80.

Unlike the prior art structure, outer sleeve 12 of the present invention is dimensioned to provide a very gradual transition between the distal end of the outer sleeve and the inner cannula. This transition is much smoother, and occurs in a much more gradual manner over a greater tapered length 14 of the outer sleeve, when compared to the much more abrupt transition of the tapered portion 104 of the prior art device shown in FIG. 1. The smooth, gradual transition at the distal end of the inventive apparatus forms a very sleek profile that enables the apparatus to be smoothly inserted into, and passed through, the initial body opening and the underlying tissue. As a result, the patient experiences reduced trauma, both at the initial insertion point and as the apparatus is further inserted into a body vessel of the patient.

Figure 6:
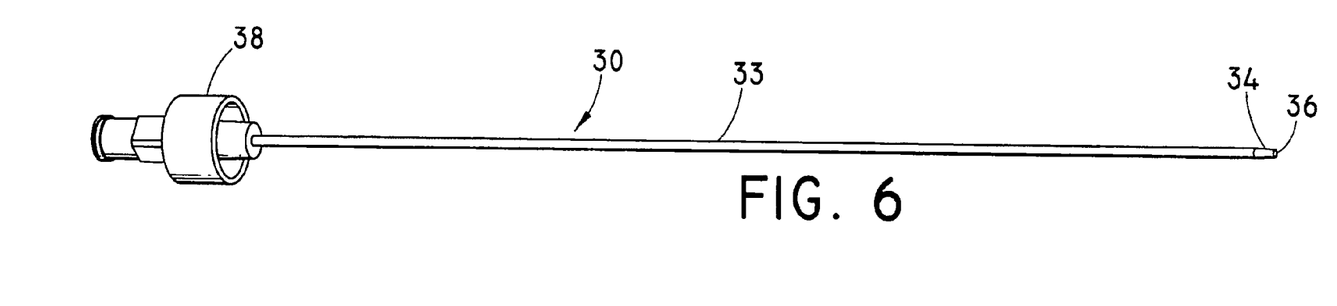
FIG. 6 illustrates a side view of the inner cannula of the low profile introducer apparatus of FIG. 3.

As best shown in FIGS. 4 and 5, outer sleeve 12 includes a main shaft portion 13, having a distal portion 14 and a proximal portion 15. Distal portion 14 tapers to outer sleeve distal end 16. The proximal end of proximal portion 15 is received within a conventional hub 18. As shown in FIG. 6, inner cannula 30 also includes a main shaft portion 33, having a distal portion 34 and a proximal portion 35. Distal portion 34 tapers to an inner cannula distal end 36. The proximal end of proximal portion 35 is received within a conventional hub 38. Respective hubs 18, 38 are sized and shaped for locking engagement when the introducer apparatus is fully assembled. Hubs 18, 38 may be of any conventional design that permits releasable engagement therebetween, the specific designs shown in the figures merely representing examples of suitable hubs. The specific design of the hubs is not germane to an understanding of the present invention, and therefore, no further description of the hubs is provided.

When introducer apparatus 10 is fully assembled as shown in FIG. 3, inner cannula 30 is received within lumen 17 of outer sleeve 12, and distal end portion 34 of inner cannula 30 extends beyond distal portion 14 of the outer sleeve. Unlike the tapered portion 104 of the outer sleeve in prior art structure 100, distal portion 14 of the outer sleeve of inventive apparatus 10 tapers in a much more gradual fashion to the distal end of the sleeve. Thus, the length c (FIG. 4) of tapered portion 14 of the inventive sleeve is longer, and in some embodiments considerably longer, than length a (FIG. 2) of the more abrupt tapered portion of a prior art device of the same outer diameter. This difference in length c when compared to length a illustrates the more gradual taper, or transition, from the outer sleeve to the inner cannula in the inventive device, when compared to the prior art structure. Preferably, the length c of the tapered portion of the inventive sleeve is between about 5 and 50 mm, more preferably between about 8 and 20 mm long.

As a result of the extended tapered length of the inventive design, the sleek profile of the inventive sleeve results in a wall thickness d of sleeve distal end 16 that is less, and in many cases considerably less, than the thickness of the wall at the distal end of the prior art design. Preferably, thickness d is between about 0.0005 and 0.003 inch [0.013 and 0.076 mm], more preferably between about 0.0005 and 0.0015 inch [0.013 and 0.38 mm], and most preferably, about 0.001 inch (±0.0005 inch) [0.025±0.013 mm]. The wall thickness of the prior art design is typically about 0.004 inch (±0.0005 inch) [0.10±0.013]. As a result, tapered distal end 14 of the inventive sleeve has a much more gradual taper than that of the prior art device, and tapers to a much narrower wall thickness at the distal end. Preferably, tapered area 14 extends at an angle not exceeding about 2° from the longitudinal axis, and preferably about 1-1.5°.

The comparative dimensions provided hereinabove are for outer sleeves of similar French sizes, and in the examples given, for a 5 French outer sleeve. In this event, length c of the inventive design is about 15 mm. This compares to length a in the prior art design of about 4 mm. For a smaller French size, such as 4 French, the length c will normally be correspondingly smaller, such as about 8 mm for the inventive design. For a larger French size, such as 6 French, the length c will normally be correspondingly larger, such as about 17 mm. For comparison, the length a of a prior art 4 French sleeve is typically about 2 mm, and the length a of a prior art 6 French sleeve is typically about 5 mm. In each case, the length of the tapered area of the prior art sleeve is significantly shorter than the length of the tapered portion of the inventive sleeve.

Those skilled in the art will appreciate that the inventive apparatus 10 can be formed to have any conventional size for its intended purposes. Preferably, the outer sleeve will generally have a diameter between about 2 and 10 French, more preferably between 4 and 6 French, and most preferably, about 5 French. However, the teachings of the present invention are also applicable to sleeves of even larger diameters, as long as the length of the sleeve can accommodate a taper as described.

The outer sleeve is preferably sized for insertion therein of inner cannulae of the type commonly used in such devices for catheterization with a small gauge needle. Thus, a conventional apparatus of the type known in the art can be utilized, with the exception of the outer sleeve, which will be dimensioned as disclosed herein. In addition to the other dimensions provided hereinabove, the lumen 15 of the outer sleeve may have a diameter similar to that of existing devices. A typical lumen diameter is about 0.04 inch (1 mm). The dimensions provided hereinabove are only examples of suitable dimensions for an outer sheath, and sheaths of other dimensions are also within the scope of the invention.

The sleek design of apparatus 10, and more particularly, of outer sleeve 12, enables the inventive apparatus to be introduced into a body vessel of a patient with a minimum of trauma. Certain tests were carried out to simulate the amount of force that a physician must exert during the insertion of the inventive introducer apparatus through the skin at a body opening. This force was compared to the amount of force that must be exerted while inserting a prior art introducer apparatus through a similar body opening. The prior art apparatus included a 5 French outer sleeve, a tapered distal sleeve portion having a length a of 4 mm and a wall thickness b at its distal end of about 0.004 inch. The tapered portion of the prior art apparatus tapered at an angle of about 3 degrees. For comparison, the inventive apparatus included a 5 French outer sleeve, a tapered distal portion having a length c of 15 mm and a wall thickness d at its distal end of about 0.001 inch. The tapered portion of the prior art apparatus tapered at an angle of about 1 degree. The inner cannulae used in each test were identical, having a diameter of 3 French and a length of about 120 mm. The length of the prior art sleeve was about 100 mm, and the length of the inventive sleeve was about 105 mm.

A sheet of 0.038 inch thick condensed silicone with a translucent color was provided to simulate the skin of a patient. Silicone sheets of this type are commercially available from, among others, AAA-Acme Rubber Company, of Tempe, Ariz., under the name Dura Silicone. In each case, the initial puncture through the silicone sheet was made with a 21 gauge needle. A 0.018 inch wire guide was inserted through the bore of the needle in conventional fashion. The needle was thereafter withdrawn over the wire guide, and the sleeve/cannula apparatus was inserted over the wire guide and through the silicone sheet.

Simulations were performed on thirty specimens of the inventive apparatus and thirty specimens of a prior art apparatus. The testing conditions were intended to be as close to identical on all specimens as possible. The tests were designed to simulate and record the maximum load (in lbf) that is exerted on the skin as the introducer apparatus initially enters the skin through the needle puncture, the compressive extension (in mm) at the maximum load encountered during insertion, and the compressive load (in lbf) at 47 mm (with the inventive apparatus) and 42 mm (with the prior art apparatus), respectively. The compressive extension at the maximum load recites the depth at which maximum force is exerted during insertion. The compressive loads at 47 and 42 mm represent readings taken past the taper and transition length. These readings indicate that the push force needed to traverse the transition between the inner cannula and the outer sleeve with the inventive design is less than the force needed to traverse the sleeve. On the other hand, with the prior art device, the push force at the point of transition considerably exceeds the force along the sleeve.

The results of the tests on the 30 specimens of the inventive apparatus are shown below in Table 1.

TABLE 1

| Specimen Label | Maximum Load (lbf) | Compressive extension at Maximum Comp. load (mm) | Compressive load at 47 mm (lbf) | Comment |
| --- | --- | --- | --- | --- |
| 1 | 0.31 | 4.47458 | 0.27933 | Pushed without incident |
| 2 | 0.35 | 4.18979 | 0.32828 | Pushed without incident |
| 3 | 0.32 | 32.73474 | 0.28809 | Pushed without incident |
| 4 | 0.40 | 36.24515 | 0.26727 | Pushed without incident |
| 5 | 0.39 | 5.53499 | 0.24153 | Pushed without incident |
| 6 | 0.33 | 5.00999 | 0.23552 | Pushed without incident |

TABLE 1-continued

| | | | | |
| --- | --- | --- | --- | --- |
| 7 | 0.36 | 35.05036 | 0.20435 | Pushed without incident |
| 8 | 0.29 | 4.70999 | 0.23899 | Pushed without incident |
| 9 | 0.28 | 47.49513 | 0.24798 | Pushed without incident |
| 10 | 0.36 | 5.23041 | 0.23015 | Pushed without incident |
| 11 | 0.35 | 41.46015 | 0.18996 | Pushed without incident |
| 12 | 0.43 | 22.76017 | 0.25893 | Pushed without incident |
| 13 | 0.37 | 5.86520 | 0.18430 | Pushed without incident |
| 14 | 0.34 | 4.84437 | 0.26116 | Pushed without incident |
| 15 | 0.29 | 46.74514 | 0.22182 | Pushed without incident |
| 16 | 0.33 | 34.20495 | 0.24218 | Pushed without incident |
| 17 | 0.35 | 5.20999 | 0.25428 | Pushed without incident |
| 18 | 0.36 | 5.63499 | 0.21307 | Pushed without incident |
| 19 | 0.36 | 5.34978 | 0.21285 | Pushed without incident |
| 20 | 0.37 | 47.17951 | 0.18557 | Pushed without incident |
| 21 | 0.36 | 46.88972 | 0.24057 | Pushed without incident |
| 22 | 0.36 | 5.47499 | 0.22677 | Pushed without incident |
| 23 | 0.38 | 6.07978 | 0.19394 | Pushed without incident |
| 24 | 0.33 | 5.61041 | 0.18142 | Pushed without incident |
| 25 | 0.28 | 4.99520 | 0.19651 | Pushed without incident |
| 26 | 0.33 | 41.46952 | 0.19551 | Pushed without incident |
| 27 | 0.39 | 5.98520 | 0.16382 | Pushed without incident |
| 28 | 0.37 | 36.46015 | 0.15755 | Pushed without incident |
| 29 | 0.38 | 5.68999 | 0.20767 | Pushed without incident |
| 30 | 0.34 | 40.59056 | 0.17002 | Pushed without incident |
| Mean | 0.35 | 19.97250 | 0.22398 | |
| Standard Deviation | 0.03480 | 17.70996 | 0.03969 | |
| Minimum | 0.28 | 4.18979 | 0.15755 | |
| Maximum | 0.43 | 47.49513 | 0.32828 | |

| | |
| --- | --- |
| Rate 1 | 150.0 mm/min |
| Data capture | Manual |
| Control mode 1 | Compressive extension |
| Start of test Temperature (deg C.) | 21.0 |
| Start of Test Relative Humidity (%) | 37.0 |
| End of test Temperature (deg C.) | 21.0 |
| End of test Relative Humidity (%) | 29.0 |

Figure 8:
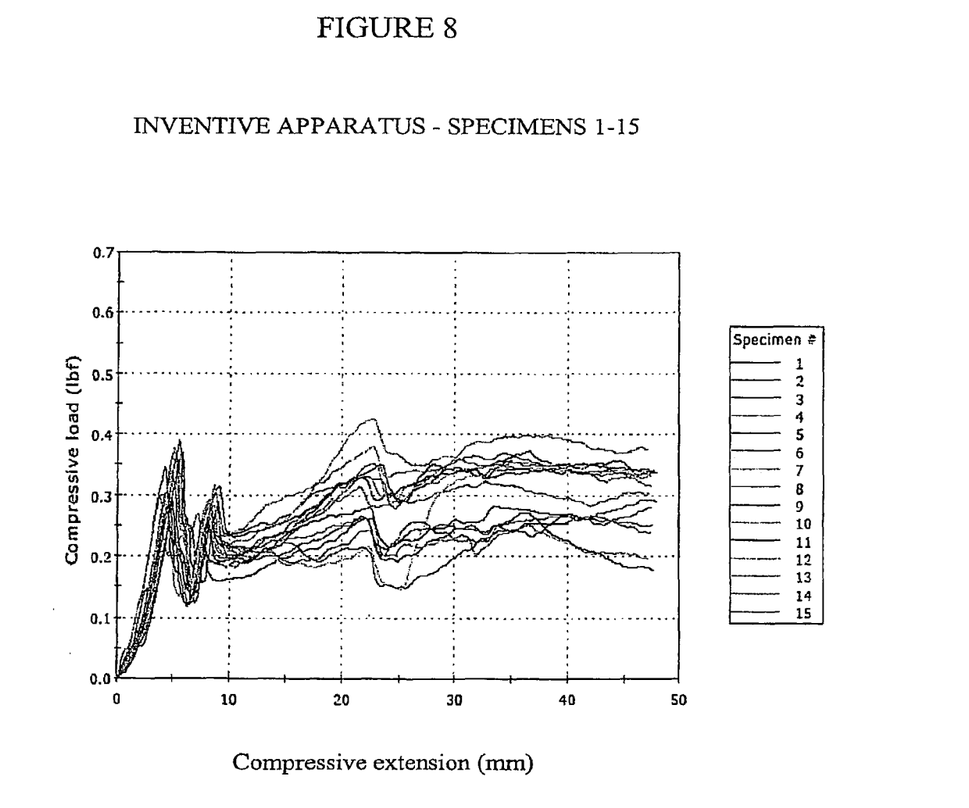
FIG. 8 is a graph illustrating the relationship between compressive extension and compressive load for specimens 1-15 of an embodiment of the inventive apparatus.
Figure 9:
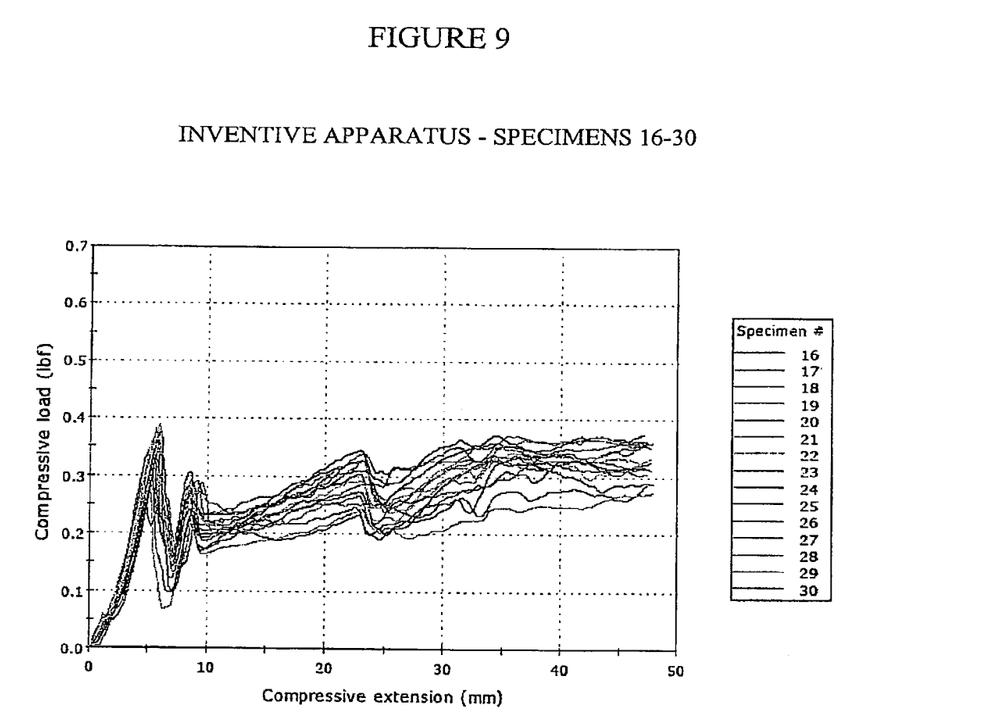
FIG. 9 is a graph illustrating the relationship between compressive extension and compressive load for specimens 16-30 of an embodiment of the inventive apparatus.

The data of Table 1 is illustrated graphically in FIG. 8 for specimens 1 to 15, and in FIG. 9 for specimens 16 to 30 of the inventive apparatus. In the figures, the "zero point" ("0") of the "compressive extension" and the "compressive load" represents the point where the inner cannula initially touches the sheet as it is urged forwardly for insertion.

The results of the tests on the 30 specimens of the conventional, prior art apparatus are shown below in Table 2.

TABLE 2

| Specimen Label | Maximum Load (lbf) | Compressive extension at Maximum Comp. load (mm) | Compressive load at 42 mm (lbf) | Comment |
| --- | --- | --- | --- | --- |
| 1 | 0.60 | 11.28040 | 0.17221 | Pushed without incident |
| 2 | 0.62 | 11.46957 | 0.13470 | Pushed without incident |
| 3 | 0.61 | 9.84978 | 0.21689 | Pushed without incident |
| 4 | 0.61 | 10.67436 | 0.17909 | Pushed without incident |
| 5 | 0.57 | 9.78998 | 0.24985 | Pushed without incident |
| 6 | 0.61 | 9.47436 | 0.28167 | Pushed without incident |
| 7 | 0.59 | 10.46415 | 0.21618 | Pushed without incident |
| 8 | 0.59 | 11.01998 | 0.14473 | Pushed without incident |
| 9 | 0.57 | 9.48040 | 0.28587 | Pushed without incident |
| 10 | 0.63 | 10.59957 | 0.19785 | Pushed without incident |
| 11 | 0.60 | 10.93436 | 0.15891 | Pushed without incident |
| 12 | 0.62 | 10.51498 | 0.18479 | Pushed without incident |
| 13 | 0.59 | 10.62915 | 0.18130 | Pushed without incident |
| 14 | 0.61 | 11.20019 | 0.16731 | Pushed without incident |
| 15 | 0.57 | 10.39457 | 0.18708 | Pushed without incident |
| 16 | 0.67 | 10.64936 | 0.22800 | Pushed without incident |
| 17 | 0.58 | 9.64540 | 0.28844 | Pushed without incident |
| 18 | 0.57 | 10.12457 | 0.21000 | Pushed without incident |
| 19 | 0.57 | 9.97436 | 0.21853 | Pushed without incident |
| 20 | 0.63 | 10.49519 | 0.20705 | Pushed without incident |
| 21 | 0.59 | 10.71936 | 0.17773 | Pushed without incident |
| 22 | 0.61 | 11.48415 | 0.12394 | Pushed without incident |

TABLE 2-continued

| | | | | |
|---|---|---|---|---|
| 23 | 0.60 | 9.99478 | 0.23544 | Pushed without incident |
| 24 | 0.60 | 10.29978 | 0.22631 | Pushed without incident |
| 25 | 0.57 | 10.59540 | 0.21824 | Pushed without incident |
| 26 | 0.57 | 10.41957 | 0.18823 | Pushed without incident |
| 27 | 0.57 | 11.18477 | 0.09785 | Pushed without incident |
| 28 | 0.53 | 9.67999 | 0.26979 | Pushed without incident |
| 29 | 0.58 | 10.18103 | 0.26243 | Pushed without incident |
| 30 | 0.62 | 10.91498 | 0.16288 | Pushed without incident |
| Mean | 0.60 | 10.47128 | 0.20244 | |
| Standard Deviation | 0.02679 | 0.57158 | 0.04818 | |
| Minimum | 0.53 | 9.47436 | 0.09785 | |
| Maximum | 0.67 | 11.48415 | 0.28844 | |

| | |
|---|---|
| Rate 1 | 150.0 mm/min |
| Data capture | Manual |
| Control mode 1 | Compressive extension |
| Start of test Temperature (deg C.) | 21.0 |
| Start of Test Relative Humidity (%) | 32.0 |
| End of test Temperature (deg C.) | 21.0 |
| End of test Relative Humidity (%) | 30.0 |

Figure 10:
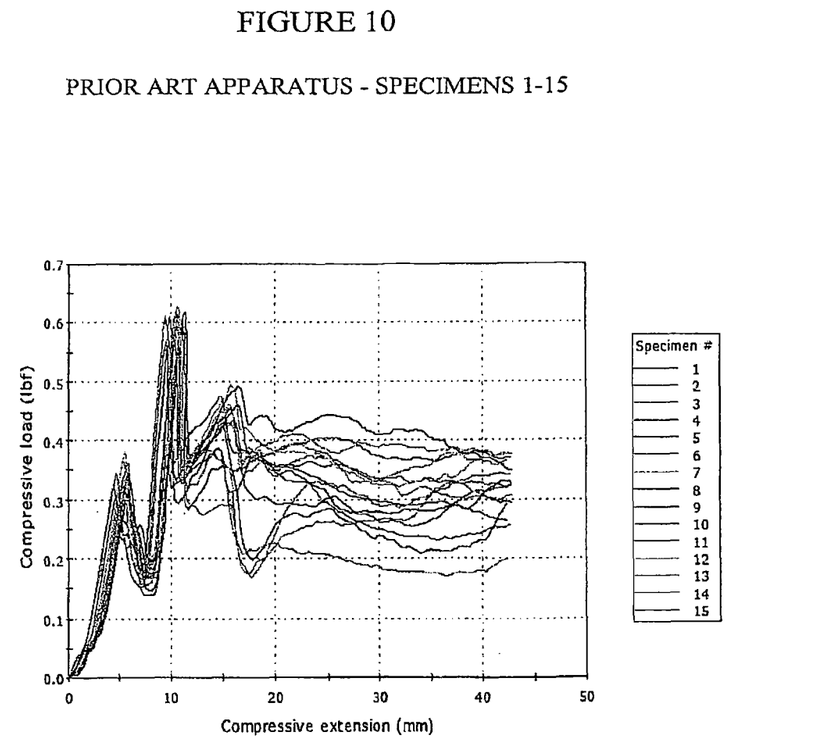
FIG. 10 is a graph illustrating of relationship between compressive extension and compressive load for specimens 1-15 of a prior art apparatus.
Figure 11:
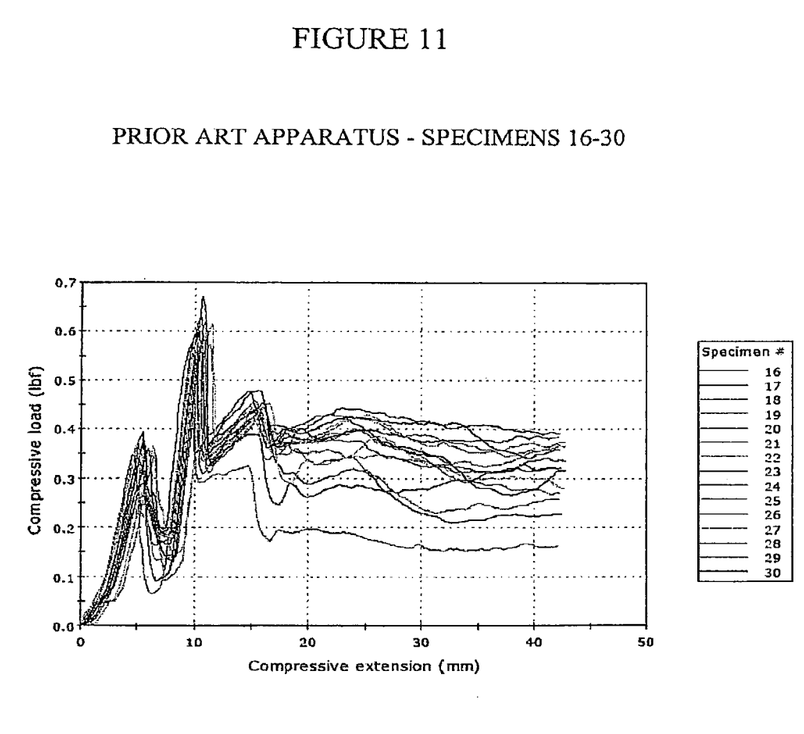
FIG. 11 is a graph illustrating the relationship between compressive extension and compressive load for specimens 16-30 of the prior art apparatus.

The data of Table 2 is illustrated graphically in FIG. 10 for specimens 1 to 15, and in FIG. 11 for specimens 16 to 30 of the prior art apparatus.

As demonstrated by the simulations, considerably more force is required to enter the skin and underlying tissue when utilizing the prior art apparatus than with the inventive apparatus. This is particularly true at the point where the distal end of the outer sleeve initially penetrates the skin. This is demonstrated in the Tables, and is graphically illustrated by the respective curves shown in FIGS. 8-11. The x-axis of the graphs represents the compressive extension, or in other words, the length of insertion (in mm) of the apparatus through the skin. The y-axis represents the compressive load, or in other words, the force (in lbf) that is exerted by the physician upon insertion of the apparatus through the skin. As shown in each of the graphs of FIGS. 8-11, the compressive load builds as the apparatus is advanced into the skin until the inner cannula has initially penetrated the skin. This is represented by the first peak in each of the figures. In both the prior art apparatus and the inventive apparatus (e.g., in each of the FIGS. 8-11), the first peak indicates a maximum compressive load that is typically between about 0.30 and 0.40 lbf.

Upon insertion of the inner cannula through the skin an immediate decrease in force is observed once the initial penetration, or puncture, has been completed. As the apparatus is further inserted, the force once again builds, to represent the force required for the outer sleeve to penetrate the skin. As illustrated in FIGS. 10 and 11 of this simulation, and as documented in Table 2, considerable force is required for the outer sleeve of the prior art apparatus to penetrate the skin. This is shown as the large (second) peak. As shown, a maximum compressive load of from about 0.53 to 0.63 lbf must typically be exerted when the outer sleeve of the prior art apparatus penetrates the skin. The mean value of maximum compressive load of all thirty prior art specimens is indicated as 0.60 lbf.

For comparison, as illustrated in FIGS. 8 and 9, and as documented in Table 1, a much smaller maximum compressive load is required when the outer sleeve of the inventive apparatus penetrates the skin. Once again, this is graphically shown by viewing the second peak in each of these figures. This peak illustrates that a compressive load of only about 0.20 to 0.30 lbf is typically required at the insertion point of the outer sleeve. The reduction in force required with the inventive apparatus when compared to the prior art apparatus is dramatically indicated by the absence of the large second peak in the inventive specimens (FIGS. 8 and 9). This indicates a much smoother insertion when compared to the prior art apparatus. The mean value of the maximum compressive load of all thirty of the inventive specimens is indicated as 0.35 lbf. In most of the inventive specimens, the maximum compressive load does not even occur at this outer sleeve insertion point (second peak), but rather, occurs either during the initial puncture, or later during the insertion procedure as the tapered outer sleeve continues to be pushed through the skin.

The inventive apparatus comprising the outer sleeve and inner cannula can be provided as a combined apparatus, or as separate components. Similarly, the remaining components discussed herein, such as the wire guide(s) and the needle, can be provided with the outer sleeve and inner cannula as a kit, or as separate components. The individual components are well known, and with the exception of the dimensional differences of the outer sleeve as described, may be formed in conventional manner and of well known compositions. Although the outer sleeve and inner cannula can be formed of any materials suitable for their intended use, preferably they will be formed from a suitable polymer well known for such use, such as polyethylene.

It is therefore intended that the foregoing detailed description be regarded as illustrative rather than limiting, and that it be understood that it is the following claims, including all equivalents, that are intended to define the spirit and scope of this invention.

The invention claimed is:

1. An introducer apparatus, comprising:
   an outer sleeve having proximal and distal open ends, and having a lumen extending longitudinally therethrough, said outer sleeve having a profile such that at least a portion of said outer sleeve tapers toward said outer sleeve distal end at an angle not exceeding about 2° relative to a longitudinal axis of the apparatus, said distal open end of said outer sleeve having a wall thickness not exceeding about 0.003 inch; and
   an inner cannula having proximal and distal open ends, and having a lumen extending longitudinally therethrough, said inner cannula sized to be received within the lumen of said outer sleeve, said inner cannula having a portion that tapers toward the inner cannula distal end, said tapered distal portion of said inner cannula extending distal to the distal open end of said outer sleeve and having a profile such that a generally smooth and gradual diametrical transition is provided from the outer sleeve tapered portion and through said inner cannula open end; and
   wherein the greatest radial extent of the inner cannula is less than the inner diameter of the outer sleeve.

2. The apparatus of claim 1, wherein said outer sleeve tapered portion comprises between about the distal 5 and 50 mm of said outer sleeve.

3. The apparatus of claim 2, wherein said outer sleeve tapered portion comprises between about the distal 8 and 20 mm of said outer sleeve.

4. The apparatus of claim 3, wherein said outer sleeve tapered portion comprises about the distal 15 mm of said outer sleeve.

5. The apparatus of claim 1, wherein said outer sleeve tapered portion is tapered at an angle of between about 0.5° and 2°.

6. The apparatus of claim 5, wherein said outer sleeve tapered portion is tapered at an angle between about 1° and 1.5°.

7. The apparatus of claim 1, wherein said distal open end of said outer sleeve has a wall thickness of between about 0.0005 and 0.0015 inch.

8. The apparatus of claim 7, wherein said distal open end of said outer sleeve has a wall thickness of about 0.001 inch.

9. The apparatus of claim 1, wherein said outer sleeve has an outer diameter not exceeding about 6 French.

10. The apparatus of claim 9, wherein said outer diameter is between about 4 and 6 French.

11. The apparatus of claim 10, wherein said diameter is about 5 French.

12. The apparatus of claim 1, wherein said apparatus is structured such that an insertion force required for insertion of said apparatus through a body vessel at a juncture of said outer sleeve distal open end and said inner cannula does not exceed an insertion force required for an initial insertion of a distal end of said inner cannula through said body vessel.

13. The apparatus of claim 1, wherein said apparatus is structured such that a lesser insertion force is required for insertion of said apparatus through a body vessel at a juncture of said outer sleeve distal open end and said inner cannula than is required for an initial insertion of a distal end of said inner cannula through said body vessel.

14. An introducer kit comprising:
a hollow thinwall needle, said needle having an outer diameter that does not exceed about 21 gauge (0.032 inch; 0.81 mm), and an inner diameter that does not exceed about 0.018 inch (0.46 mm);
a first wire guide, said first wire guide having an outer diameter not less than about 0.035 inch (0.89 mm);
a second wire guide, said second wire guide receivable in a bore of said needle;
an outer sleeve, said outer sleeve having proximal and distal open ends and having a lumen extending longitudinally therethrough, said outer sleeve having a profile such that a distal portion of said outer sleeve tapers toward said outer sleeve distal end at an angle not exceeding about 2° relative to a longitudinal axis of the apparatus, said outer sleeve tapered portion comprising between about the distal 8 and 20 mm of said outer sleeve, said outer sleeve having an outer diameter that does not exceed about 6 French and having a distal open end sized such that said first wire guide is receivable therethrough, said distal end of said outer sleeve having a wall thickness between about 0.0005 and 0.0015 inch; and
an inner cannula, said inner cannula having proximal and distal open ends and having a lumen extending longitudinally therethrough, said inner cannula sized to be received within the lumen of said outer sleeve, said inner cannula having a portion that tapers toward the inner cannula distal end, said tapered distal portion of said inner cannula extending distal to the distal open end of said outer sleeve and having a profile such that a generally smooth and gradual diametrical transition is provided from the outer sleeve tapered portion and through said inner cannula open end; and
wherein the greatest radial extent of the inner cannula is less than the inner diameter of the outer sleeve.

15. The kit of claim 14, wherein said outer sleeve tapered portion comprises the distal 15 mm of said outer sleeve.

16. The kit of claim 15, wherein said distal open end of said outer sleeve has a wall diameter of about 0.001 inch (0.0254 mm).

17. The kit of claim 16, wherein said outer sleeve has an outer diameter that does not exceed about 5 French.

18. A method of inserting a wire guide into a body vessel of a patient for use in introducing a medical interventional device, comprising:
providing an introducer system, said system comprising an introducer needle having an outer diameter that does not exceed about 21 gauge (0.032 inch; 0.81 mm) and an inner diameter that does not exceed about 0.018 inch (0.46 mm); a first wire guide having an outer diameter not less than about 0.035 inch (0.89 mm); a second wire guide having an outer diameter not greater than about 0.018 inch (0.46 mm) and being receivable in a bore of said introducer needle; and an introducer apparatus comprising an outer sleeve and an inner cannula, said inner cannula removably received in a lumen of said outer sleeve, said outer sleeve having proximal and distal open ends and a profile such that a distal portion of said outer sleeve tapers toward said sleeve distal end at an angle not exceeding about 2° with a longitudinal axis of the sleeve, said outer sleeve distal open end sized such that said first wire guide is receivable therethrough, said inner cannula having proximal and distal open ends and a lumen extending therethrough, and having a portion that tapers toward the inner cannula distal end, said tapered distal portion of said inner cannula extending distal to the distal open end of said outer sleeve and having a profile such that a generally smooth and gradual diametrical transition is provided from the outer sleeve tapered portion and through said inner cannula open end; and
wherein the greatest radial extent of the inner cannula is less than the inner diameter of the outer sleeve;
injecting said needle into said body vessel;
guiding said second wire guide through said needle bore such that a distal end of said wire guide extends beyond said needle in said body vessel;
withdrawing said needle from said body vessel over said second wire guide;
introducing said introducer apparatus over said second wire guide such that the respective distal ends of said outer sleeve and inner cannula are in said body vessel;
wherein said introducing step comprises inserting said distal end of said inner cannula into said body vessel at a first insertion force, and inserting said introducer apparatus at a juncture of said outer sleeve distal open end and said inner cannula at a second insertion force, such that said second insertion force does not exceed said first insertion force;
withdrawing said second wire guide from said introducer apparatus while maintaining the introducer apparatus in the body vessel;
separating the inner cannula from the outer sleeve, and removing the inner cannula while maintaining the outer sleeve in the body vessel; and
guiding said first wire guide through said outer catheter such that a distal end of said first wire guide extends beyond said outer sleeve in said body vessel.

19. The method of claim 18, further comprising:
withdrawing said outer cannula over said first wire guide.

20. The method of claim 18, wherein said angle is about 1°.

21. The method of claim 20, wherein said distal open end of said outer catheter has a thickness less than about 0.003 inch.

22. The method of claim 20, wherein said distal open end of said outer catheter has a thickness of about 0.001 inch.

* * * * *